United States Patent [19]

Potter

[11] Patent Number: 4,469,477
[45] Date of Patent: Sep. 4, 1984

[54] DENTAL PROSTHESIS

[75] Inventor: William D. Potter, Bishops Stortford, England

[73] Assignee: Smith & Nephew Associated Companies p.l.c., England

[21] Appl. No.: 478,241

[22] Filed: Mar. 24, 1983

[30] Foreign Application Priority Data

Apr. 2, 1982 [GB] United Kingdom ............ 8209777

[51] Int. Cl.$^3$ .................................... A61K 6/08
[52] U.S. Cl. ............................ 433/168; 433/171; 433/199; 433/201; 523/120
[58] Field of Search ............... 433/168, 171, 199, 201; 264/17; 523/120

[56] References Cited

U.S. PATENT DOCUMENTS

| | | | |
|---|---|---|---|
| 3,822,238 | 7/1974 | Blair et al. | 433/199 |
| 3,930,076 | 12/1975 | Kliment | 427/353 |
| 4,088,500 | 5/1978 | Fairbanks et al. | 106/35 |
| 4,251,215 | 2/1981 | May et al. | 433/168 |

FOREIGN PATENT DOCUMENTS 2027043 2/1980 United Kingdom .
2093190 8/1982 United Kingdom .

OTHER PUBLICATIONS

Bezc., J. Pros. Dent., 1970, 23 (4), pp. 396-406.

Primary Examiner—Lorenzo B. Hayes
Attorney, Agent, or Firm—Jacobs & Jacobs

[57] ABSTRACT

A dental prosthesis which has the whole or part of its surface which is in contact with the mucous membrane of the mouth coated with a soft, hydrophilic polyurethane is provided. The polyurethane coating has a thickness of from 0.1 to 3.00 mm when hydrated. The polyurethane is applied to the prosthesis from a non-aqueous solvent in an anhydrous state and is subsequently hydrated by soaking in water. The polyurethane is a reaction product of a mixture of polyether polyols and a di-isocyanate using an alkenediol as a chain extender. The polyurethane contains from 5 to 40% water when hydrated.

7 Claims, No Drawings

DENTAL PROSTHESIS

The present invention relates to a dental prosthesis which is coated on the surface which is in contact with the mucous membranes of the mouth with a soft polymeric lining and to a process for forming the coating on such surfaces of a prosthesis.

It has long been recognised by the dental profession that difficulties may arise in the permanent fitting of dental prostheses due to sensitive oral mucosa or to oral skeletal changes after removal of natural teeth. These difficulties and the properties required of an idealized soft or resilient polymeric denture liner have been discussed in relation to a hydrophilic polyhydroxyethylmethacrylate liner (see Clinical Evaluation of a Resilient Denture Liner, D. H. Bell, J. Pros. Dent. 1970, 23 (4) 396–406). Further attempts to develop a soft polymeric denture liner possessing the features described in the above paper are disclosed in for example U.S. Pat. Nos. 3,930,076, 4,088,500, 4,251,125, British patent application No. 2027043A and West German Offenlegungschrift No. 2718818. To this date no soft polymeric denture liner has completely fulfilled these properties or mitigated the difficulties associated with dental prostheses and their liners. However it has now been discovered that if the dental prosthesis is coated with a soft hydrophilic polyurethane then many of these outstanding difficulties regarding adhesion of the liner to the prosthesis and the inertness and stability of the liner in the oral environment are mitigated.

Accordingly the present invention provides a dental prosthesis in which the whole or part of the surface which is in contact with the mucous membrane of the mouth is coated with a soft polymeric lining characterised in that the soft polymeric lining comprises a coating of hydrophilic polyurethane having a thickness of 0.1 to 3.0 mm when hydrated.

In a preferred aspect of the invention the hydrophilic polyurethane will be coated onto those parts of the dental prosthesis which provide pressure contact of the dental prosthesis against the gums and jawbone as well as against the palate of the wearer. These surfaces are known as the tissue bearing surfaces of the dental prosthesis as distinct from the non-pressure bearing surfaces which contact the side or lips of the wearer's mouth. In a preferred embodiment therefore only the tissue bearing surfaces will be coated with the hydrophilic polyurethane.

The thickness of the coating is suitably from 0.1 mm to 3.0 mm and is preferably 0.5 to 2.5 mm when hydrated. The thickness of the coating will depend on its ability to provide a cushioning effect. At a thickness below 0.1 mm the coating does not provide adequate cushioning to the tissue bearing surfaces and may be too fragile to withstand robust treatment during use, for example when cleaning. At a thickness of above 3.00 mm the lining may be uncomfortable in wear, difficult to apply to build up such a large coating and tend to accumulate food debris and the like on its surface which is not easily removed during cleaning. The thickness of the coating here is defined in terms of that present on the tissue bearing surfaces. If the coating is applied to a non-tissue bearing surface as well it would be expected to be thinner than that on the tissue bearing surfaces.

Suitably the hydrophilic polyurethane used to form the soft polymeric liner is a linear polyether polyurethane. The preparation of such polyurethanes is described in our copending British Application No. 8,130,887, now published as U.K. patent application No. 2093190A which is incorporated herein by cross reference. This application describes the use of such polyurethanes as blood gas permeable membranes on electrochemical sensors. However the thickness of the membrane used in such devices is significantly thinner than that use as a lining for a dental prosthesis of the present invention.

Particularly apt hydrophilic polyurethanes are those which when hydrated contain 10 to 40% water and preferably contain from 20 to 30% water. It has been found that polyurethanes of such a water content provide a suitable degree of softness together with satisfactory biocompatibility and adhesion to the palate or gums.

Aptly the ether blocks of the linear polyether polyurethane will be notionally derived from ethylene diol and propylene diol or butylene diol mixtures. Desirably the mole ratio of such derived poly(ethylene glycol) to poly[(prop- or but)ylene glycol] blocks present in the hydrophilic polyurethane will vary between 1:2 to 1:10.

Most aptly the hydrophilic polyurethane for use in this invention will contain residues of aliphatic diols of up to 10 carbon atoms, of which ethane diol is preferred as chain extenders wherein the mole ratio of diol to polyglycol derivable block is from 3:1 to 1:4 and preferably 5:2 to 1:3.

The hydrophilic polyurethane will contain sufficient of di-isocyanate residues to produce the water content as hereinbefore defined when the polymer is hydrated.

Most aptly the di-isocyanate residues contained in the hydrophilic polyurethane will be derived from aromatic or aliphatic di-isocyanates such as 4,4'-diphenylmethane di-isocyanate, toluene di-isocyanate, 1,6 hexamethylene di-isocyanate, 4,4'dicyclohexylmethane di-isocyanate and the like.

Suitably the polymer may be applied to the dental prosthesis by any convenient method of coating surfaces such as dip coating, spraying, painting or the like. The hydrophilic polyurethane is dissolved in a suitable solvent in such processes. Usually the dental prosthesis is made from either polymethyl methacrylate or a copolymer of vinyl chloride and vinyl acetate. To coat the prosthesis the hydrophilic polyurethane will be dissolved in a solvent which generally does not affect the polymer of the dental prosthesis. Such solvents include alkanols such as methanol, ethanol and the like. A preferred solvent is ethanol. However it is advantageous to include in the solvent for the polyurethane a small amount of a solvent, for example up to 5% for the prosthesis material. This small amount of solvent will dissolve the polymer at the surface of the prosthesis and promote mixing at the liner-prosthesis interface thereby increasing the adhesion between the liner and the prosthesis. Suitable a small amount of halogenated hydrocarbon will be used with polymethylmethacrylate prostheses and tetrahydrofuran for the polyvinyl chloride-polyvinyl acetate copolymer. Suitably the solution of polyurethane will contain from 1 to 15% w/w of the polyurethane and preferably 2.5 to 5% w/w.

In a second aspect therefore the present invention provides a process for coating a surface of a dental prosthesis with a soft polymeric lining material comprising a hydrophilic polyurethane as herein described.

Normally the coating of hydrophilic polyurethane will be applied to form an anhydrous coating. Suitably the coating will be hydrated by standing the coated prosthesis in aqueous solution for a time sufficient to completely hydrate the polymer. Preferably the coating will be hydrated using an isotonic aqueous solution which has been buffered to a pH value of between 6.5 and 7.5, for example 7.2, using a buffer comprising a mixture of phosphate salts known to give such pH values. Suitably the coated dental prosthesis will be soaked for 48 hours in this solution, the solution being at a temperature of approximately 37° C.

Acrylic denture bases which were coated by painting with a methanolic solution of a hydrophilic polyurethane, as hereinafter described, were soaked for up to six months in phosphate-buffered saline at pH 7.2 and 37° C. The denture bases were assessed periodically for coating integrity and discolouration. No deterioration or discolouration of the coating was observed.

Dental prosthesis are conventionally cleaned each day either by soaking in a solution of a perborate salt for 10 minutes or by soaking in a solution of a hypochlorite salt for 20 minutes. The acrylic denture bases which has been soaked for six months above were exposed to one or other of the systems for 24 hours continuous soaking. In all cases after treatment the coating was intact, attached to the acrylic strip, was not discoloured and had no taste of the cleaning material.

A further test was carried out in which the coated acrylic strips were soaked in black tea or black coffee for 24 hours. The coating was stained by both solutions. The stain could not be removed by merely rinsing with water. Conventional cleaning using a hypochlorite solution markedly lightened the tea stain. Both types of stain were removed by overnight soaking in hypochlorite solution. The coating was not affected by the treatment.

These tests show that the coatings used in the invention are suitable for use as denture liners.

In use the liner will not be visible, however it may be aesthetically pleasing to colour the liner to a red or pink flesh colouration. Suitably the pigment will be included in the coating solution. Most aptly the pigments used will be those known to be non-toxic when used in medical devices in contact with the human body. Suitable red colours include DC No. 30 Red Lake K7156, Atlas Colours. The amount of colour used is aptly 0.02 to 0.05% based on the weight of polyurethane used.

Optionally the liner may also include an inert filler. Suitably this filter is a finely divided silica, for example Aerosil Type 380, available from Degussa. Other organic and inorganic materials may be used as inert fillers. These include hydrated alumina, diatomaceous earth, bentonite clay, Fullers earth, calcium carbonate and the like. The filler suitably has a particle size of 0.1 to 100 microns and is present at between 3 and 10% by weight based on the weight of the polyurethane.

Alternatively the liner may be preformed by coating onto a plaster of paris impression of the palate or gums of the prospective wearer of the denture, removal from the impression and the unhydrated polyurethane liner pressed or adhered to the dental prosthesis prior to hydration. Preferably the liner will be adhered to the prosthesis using a conventional acrylic bonding primer.

Preparation of Hydrophilic Polyurethane

A mixture of the following:

| | |
|---|---|
| Polyethylene glycol 1540 | 15.4 g (0.01 mole) |
| Polypropylene glycol 1025 | 30.75 g (0.03 mole) |
| Ethane diol | 3.71 g (0.06 mole) |
| Di-butyl tin dilaurate | 0.15 g | is heated in a beaker to 50° C. on a hot plate with constant stirring. 4,4,'dicyclohexyl methane di-isocyanate (27.5 g, 0.11 mole) is added to the mixture which is stirred for 30 seconds when the mixture became clear. The mixture is immediately poured into a mould (high density polyethylene) and is placed in an oven at 70° C. for 1 hour. After removal from the oven the resulting hydrophilic polyurethane is left for at least 24 hours before use. This material will have a water uptake of about 26%.

EXAMPLE 1

Preparation of Lined Dental Prosthesis

A portion of a hydrophilic polyurethane prepared as described above is dissolved in ethanol to form a 10% solution. This solution is painted on to the tissue bearing surfaces of a conventional polymethyl methacrylate dental prosthesis and the solvent allowed to evaporate. By repetition of this procedure a coating of appropriate thickness of unhydrated polyurethane is thereby left on the tissue bearing surfaces. The denture and lining are then immersed in a phosphate-buffered saline solution, pH value 7.2, for 48 hours at 37° C. After this period the polyurethane is hydrated and provides a soft, resilient, stable and well adhered lining for the denture.

EXAMPLE 2

Preparation of Lined Dental Prosthesis

A portion of a hydrophilic polyurethane prepared by the same method described above is dissolved in methanol sufficient to form a 5% solution. This solution is painted onto the tissue bearing surfaces of a conventional polymethyl methacrylate dental prosthesis and the solvent allowed to evaporate. By repetition of this procedure a coating of appropriate thickness of unhydrated polyurethane is thereby left on the tissue bearing surfaces. The swell factor of the polyurethane is determined by measuring the dimensions of a sample of the polyurethane before and after hydrating in a phosphate-buffered saline solution at pH 7.2. Thus by inspecting the layer of unhydrated polyurethane as it is built up the appropriate hydrated thickness may be calculated. The inspection may be carried out by measurement of a cross-section at the end of the prosthesis using a microscope. The swell factor of the polyurethane used is 1.12. After coating, the denture and lining are then immersed in a phosphate-buffered saline solution, pH value 7.2, for 48 hours at 37° C. At the end of this period of polyurethane is hydrated and provides a soft, resilient, stable and well adhered lining for the denture.

Demonstration of Effectiveness

The adhesive qualities of the hydrated polyurethane material to the dental prosthesis material was shown by testing according to British Standard BS 5350 Part C10 1979, which measures the peel strength of a prepared bond line by pulling a flexible adherent in a direction normal to the surface of a rigid adherent.

In the unhydrated condition the polyurethane material failed cohesively.

In the hydrated condition the polyurethane material adhered without acrylic primer showed a peel strength of 25 Newtons, whilst the polyurethane material adhered additionally with primer showed a peel strength of 32 Newtons. In neither did the polyurethane fail cohesively.

A comparative test with a conventional liner showed it to fail cohesively after hydration.

The test illustrates the good adhesion between the dental prosthesis and its liner when in the hydrated state.

A similar series of tests according to British Standard BS 5350 Part C10 1979 were carried out on polymethyl methacrylate strips coated with hydrophilic polyurethane from methanolic solution and hydrated and allowed to stand for three months in tap water at room temperature. The polyurethane layer was then peeled from the acrylic strip using an Instron tensile testing machine at a cross-head speed of 1 mm/min. The peel strength was measured. The results showed a reduction in peel strength compared to the results obtained immediately after hydration but were still higher than those obtained for a conventional liner and acrylic strip even when measured immediately after such a strip had been hydrated and the adhesive forces should be at their highest. The test strips showed adhesive and not cohesive failure.

These results illustrate that the adhesion between the prosthesis material and its liner is high even after prolonged soaking.

What is claimed is:

1. A dental prosthesis having at least part of the surface of the prosthesis which contacts the mucous membrane of the mouth coated with a soft polymeric lining characterized in that the soft polymeric lining is produced by coating the prosthesis with a hydrophilic linear polyether polyurethane and hydrating the coating with water to a thickness of 0.1 to 3.0 mm and a water content of 20 to 30%.

2. A dental prosthesis as claimed in claim 1 in which the coating has a thickness of 0.5 to 2.5 mm.

3. A dental prosthesis as claimed in claim 1 in which the ether units of the hydrophilic linear polyether polyurethane contain poly(ethylene) glycol derivable blocks and poly[(prop- or but-)ylene] glycol derivable blocks in the mole ratio of 1:2 to 1:10 and ethane diol wherein the mole ratio of ethane diol to polyglycol derivable blocks is from 5:2 to 1:3.

4. A dental prosthesis as claimed in claim 3 in which the hydrophilic linear polyether polyurethane employs 4,4'-dicyclohexyl methane di isocyanate.

5. A dental prosthesis as claimed in claim 1 wherein the coating is applied to the surface of the prosthesis by painting from a solution of the hydrophilic linear polyether polyurethane.

6. A process for coating a surface of a dental prosthesis with a soft polymeric lining material which comprises applying to the surface a hydrophilic linear polyether polyurethane from an anhydrous solution of the polymer and hydrating the polyurethane to form a layer 0.1 to 3.0 mm thick and containing 20 to 30% water.

7. A process as claimed in claim 6 in which the hydrophilic linear polyether polyurethane is applied to the surface by painting from an ethanolic solution of the hydrophilic polyurethane which contains from 1 to 15% of said polyurethane.

* * * * *